US010717828B2

(12) United States Patent
Gabbay

(10) Patent No.: US 10,717,828 B2
(45) Date of Patent: Jul. 21, 2020

(54) ANTIMICROBIAL AND ANTIVIRAL POLYMERIC MASTER BATCH, PROCESSES FOR PRODUCING POLYMERIC MATERIAL THEREFROM AND PRODUCTS PRODUCED THEREFROM

(71) Applicant: THE CUPRON CORPORATION, Greensboro, NC (US)

(72) Inventor: Jeffrey Gabbay, Jerusalem (IL)

(73) Assignee: Cupron Inc., Richmond, VA (US)

(*) Notice: Subject to any disclaimer, the term of this patent is extended or adjusted under 35 U.S.C. 154(b) by 585 days.

(21) Appl. No.: 14/685,005

(22) Filed: Apr. 13, 2015

(65) Prior Publication Data

US 2015/0218321 A1 Aug. 6, 2015

Related U.S. Application Data

(62) Division of application No. 11/908,771, filed as application No. PCT/IL2006/000320 on Mar. 12, 2006.

(30) Foreign Application Priority Data

Mar. 21, 2005 (IL) .......................................... 167564
Mar. 1, 2006 (IL) .......................................... 174021

(51) Int. Cl.
C08J 3/22 (2006.01)
A01N 59/20 (2006.01)
A61L 29/12 (2006.01)
C08L 67/04 (2006.01)
A61L 29/16 (2006.01)
A61L 31/16 (2006.01)
C08L 67/02 (2006.01)
C08L 91/06 (2006.01)
C08J 3/20 (2006.01)
D01F 1/10 (2006.01)
A61L 31/12 (2006.01)
C08K 3/22 (2006.01)
C08K 5/00 (2006.01)
(Continued)

(52) U.S. Cl.
CPC ................ C08J 3/22 (2013.01); A01N 59/20 (2013.01); A61L 29/126 (2013.01); A61L 29/16 (2013.01); A61L 31/128 (2013.01); A61L 31/16 (2013.01); C08J 3/201 (2013.01); C08K 3/22 (2013.01); C08K 5/0008 (2013.01); C08L 67/02 (2013.01); C08L 67/04 (2013.01); C08L 91/06 (2013.01); D01F 1/10 (2013.01); A61B 42/00 (2016.02); A61B 46/40 (2016.02); A61B 2017/00889 (2013.01); A61F 2013/49098 (2013.01); A61L 2300/102 (2013.01); A61L 2300/404 (2013.01); C08J 2323/02 (2013.01); C08J 2323/06 (2013.01); C08J 2323/08 (2013.01); C08J 2323/12 (2013.01); C08J 2323/14 (2013.01); C08J 2323/20 (2013.01); C08J 2327/06 (2013.01); C08J 2327/18 (2013.01); C08J 2333/00 (2013.01); C08J 2367/00 (2013.01); C08J 2367/04 (2013.01); C08J 2375/04 (2013.01); C08J 2377/00 (2013.01); C08J 2400/22 (2013.01); C08J 2491/06 (2013.01); C08K 2003/2248 (2013.01)

(58) Field of Classification Search
CPC . C08J 3/22; C08J 3/201; C08J 2323/02; C08J 2323/06; C08J 2323/08; C08J 2323/12; C08J 2323/14; C08J 2323/20; C08J 2327/06; C08J 2327/18; C08J 2333/00; C08J 2367/00; C08J 2367/04; C08J 2375/04; C08J 2377/00; C08J 2400/22; C08J 2491/06; A01N 59/20; A61L 29/126; A61L 29/16; A61L 31/128; A61L 31/16; A61L 2300/404; A61L 2300/102–104; C08L 67/02; C08L 67/04; C08L 91/06; D01F 1/10; A61B 42/00; A61B 46/40; A61B 2017/00889; A61F 2013/49098; C08K 2003/2248; C08K 3/104
See application file for complete search history.

(56) References Cited

U.S. PATENT DOCUMENTS 4,592,920 A * 6/1986 Murtfeldt ................ A61L 29/16
427/2.25
4,603,152 A * 7/1986 Laurin .................... A01N 25/10
604/265
(Continued)

FOREIGN PATENT DOCUMENTS

JP 2000159898 * 6/2000 ................ C08J 3/22
WO 2014130431 A2 8/2014

OTHER PUBLICATIONS

Zhanhu Guo et al., "CuO nanoparticle filled vinyl-ester resin nanocomposites: Fabrication, characterization and property analyses"; Composites Science and Technology, vol. 67, No. 10, May 9, 2007, pp. 2036-2044.

(Continued)

Primary Examiner — Matthew J Daniels
Assistant Examiner — Andrew L Swanson
(74) Attorney, Agent, or Firm — Bernard G. Pike; Pike IP Law, PLLC

(57) ABSTRACT

A polymeric master batch for preparing an antimicrobal and antifungal and antiviral polymeric material comprising a slurry of thermoplastic resin, an antimicrobal and antifungal and antiviral agent consisting essentially of water insoluble particles of ionic copper oxide, a polymeric wax and an agent for occupying the charge of the ionic copper oxide.

9 Claims, No Drawings

(51) Int. Cl.
*A61B 17/00* (2006.01)
*A61F 13/49* (2006.01)
*A61B 42/00* (2016.01)
*A61B 46/00* (2016.01)

(56) References Cited

U.S. PATENT DOCUMENTS

| | | | | |
|---|---|---|---|---|
| 5,077,328 A | * | 12/1991 | Haruna | C08K 5/103 524/100 |
| 5,180,585 A | * | 1/1993 | Jacobson | A01N 25/26 424/404 |
| 5,475,123 A | * | 12/1995 | Bos | C07C 29/70 556/130 |
| 5,894,042 A | * | 4/1999 | Ferralli | B05D 7/02 138/145 |
| 5,997,829 A | | 12/1999 | Sekine et al. | |
| 7,445,799 B1 | * | 11/2008 | Sarangapani | A01N 59/16 424/404 |
| 2002/0106413 A1 | * | 8/2002 | Herbst | A01N 31/08 424/600 |
| 2004/0247653 A1 | * | 12/2004 | Gabbay | A01N 57/20 424/443 |
| 2005/0048131 A1 | | 3/2005 | Gabbay | |
| 2005/0049370 A1 | | 3/2005 | Gabbay | |
| 2012/0171276 A1 | | 7/2012 | Fujimori et al. | |

OTHER PUBLICATIONS

S. Rodriguez-Llamazares et al., "PVC/Copper oxide composites and their effect on bacterial adherence"; Journal of the Chilean Chemical Society, vol. 57, No. 2, Jan. 1, 2012, pp. 1163-1165.
Extended European Search Report for European counter application No. 13827838.7-1454 / 2882295 PCT/US2013054040 dated Mar. 15, 2016.

* cited by examiner

ANTIMICROBIAL AND ANTIVIRAL POLYMERIC MASTER BATCH, PROCESSES FOR PRODUCING POLYMERIC MATERIAL THEREFROM AND PRODUCTS PRODUCED THEREFROM

This application is a divisional of U.S. application Ser. No. 11/908,771 filed on Apr. 1, 2008, which is a national stage entry of International Application No. PCT/IL2006/00320 filed on Mar. 12, 2006, each of which is incorporated by reference in its entirety.

The present invention relates to an antimicrobial and antiviral polymeric master batch, to processes for producing antimicrobial and antiviral polymeric materials therefrom and to products produced therefrom. More particularly, the present invention relates to an improved process and master batch for preparing antimicrobial and antiviral polymeric materials having a multitude of uses.

As described in US2004/0247653 by the present inventor, a problem faced by all food exporters is the attack on the agricultural produce after it has been harvested, by microorganisms while in transport. This is especially true when the transportation is measured in days, weeks, or months, rather than hours. Microorganisms are known to cause severe damage to the produce, resulting in added costs that are passed on to the consumer. An example of this is the strawberry harvest in Israel. Every year about 50% of the harvest is lost while in transportation due to the attack of microorganisms. To date, there has been no effective system developed that can effectively reduce the waste rate.

There are many wrapping materials used in food transport from burlap bags to sophisticated polymer wrappings that demonstrate qualities such as strength, flexibility, breathability and are inexpensive. However, none to date are able to control the growth of microorganisms that flourish in packaged, agricultural produce.

According to the invention described therein it has now been discovered that by adding a small percentage of Cu++ in the form of water insoluble copper oxide particles to the slurry of a polymer to be formed into a wrapping material, the package is rendered antimicrobial, antiviral and antifungal. Thus, such polymeric film could be used for bags for the food industry, produce bags, flower bags, anti-mold seed bags and even as a layer in body bags.

Furthermore as described therein it has been surprisingly discovered that by adding copper oxide in particle form into a polymeric slurry of such polymers as polyethylene, polypropylene, polyesters and similar thermoplastic polymeric materials it is possible to extrude fibers, yarns or sheets which possess antimicrobial, antifungal and antiviral properties which have a multiplicity of uses. Among the uses contemplated for said antimicrobial and antiviral polymeric materials is their use in a backing for a carpet, which could even be used in a hospital setting since it would not develop mold, smell, and would inactivate any viruses settling thereon; the use as a component of a molded non-woven product such as an air filter in a hospital or airplane or a mask which could be made air permeable or liquid permeable and be used to filter fluids flowing therethrough and to inactivate bacteria and viruses found in said fluids; formation into a continuous, flat, textured or stretched form which could be used in articles of clothing such as stockings, socks, shirts or any article of clothing that would incorporate a hydrophobic polymeric fiber or yarn; formation of a short staple fiber which could be then used as is or blended with other fibers such as cotton, which blended yarns could then be used for the manufacture of a variety of both knit and woven products such as socks, sheets, etc.; and use of such polymeric materials, manufactured in the form of a bi-component yarn in which the core is one compound and the sheath around the core is a polymer containing the water insoluble copper oxide particles creating a yarn with a multitude of end uses in either a continuous, flat, textured, stretched form or as a short staple, extruded into a polymeric non-woven substrate or fabric. An example of said latter use would be the use of a polyethylene core with a polymeric sheath incorporating said water insoluble copper oxide particles to form a yarn with an increased resistance to being cut or ripped while also being both antimicrobial and antiviral and having a multiplicity of uses including in the food preparation industry. Further a hydrophilic polymeric fiber of yarn or material could be created from the hydrophobic material using any one of the commercial components available for this such as Burlington Industries Inc. Nano-Tech finish compounds.

In both WO 98/06508 and WO 98/06509 there are taught various aspects of a textile with a full or partial metal or metal oxide plating directly and securely bonded to the fibers thereof, wherein metal and metal oxides, including copper, are bonded to said fibers.

More specifically, in WO 98/06509 there is provided a process comprising the steps of: (a) providing a metallized textile, the metallized textile comprising: (i) a textile including fibers selected from the group consisting of natural fibers, synthetic cellulosic fibers, regenerated fibers, acrylic fibers, polyolefin fibers, polyurethane fibers, vinyl fibers, and blends thereof, and (ii) a plating including materials selected from the group consisting of metals and metal oxides, the metallized textile characterized in that the plating is bonded directly to the fibers; and (b) incorporating the metallized textile in an article of manufacture.

In the context of said invention the term "textile" includes fibers, whether natural (for example, cotton, silk, wool, and linen) or synthetic yarns spun from those fibers, and woven, knit, and non-woven fabrics made of those yarns. The scope of said invention includes all natural fibers; and all synthetic fibers used in textile applications, including but not limited to synthetic cellulosic fibers (i.e., regenerated cellulose fibers such as rayon, and cellulose derivative fibers such as acetate fibers), regenerated protein fibers, acrylic fibers, polyolefin fibers, polyurethane fibers, and vinyl fibers, but excluding nylon and polyester fibers, and blends thereof.

Said invention comprised application to the products of an adaptation of boards made of plastic, with metals. See, for example, Encyclopedia of Polymer Science and Engineering (Jacqueline I. Kroschwitz, editor), Wiley and Sons, 1987, vol. IX, pp 580-598. As applied to textiles, this process included two steps. The first step was the activation of the textile by precipitating catalytic noble metal nucleation sites on the textile. This was done by first soaking the textile in a solution of a low-oxidation-state reductant cation, and then soaking the textile in a solution of noble metal cations, preferably a solution of Pd++ cations, most preferably an acidic $PdCl_2$ solution. The low-oxidation-state cation reduces the noble metal cations to the noble metals themselves, while being oxidized to a higher oxidation state. Preferably, the reductant cation is one that is soluble in both the initial low oxidation state and the final high oxidation state, for example Sn++, which is oxidized to Sn++++, or Ti+++, which is oxidized to Ti++++.

The second step was the reduction, in close proximity to the activated textile, of a metal cation whose reduction was catalyzed by a noble metal. The reducing agents used to reduce the cations typically were molecular species, for example, formaldehyde in the case of Cu++. Because the reducing agents were oxidized, the metal cations are termed "oxidant cations" herein. The metallized textiles thus produced were characterized in that their metal plating was bonded directly to the textile fibers.

In WO 98/06508 there is described and claimed a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plating including materials selected from the group consisting of metals and metal oxides;
the composition of matter characterized in that said plating is bonded directly to said fibers.

Said publication also claims a composition of matter comprising:
(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and
(b) a plurality of nucleation sites, each of said nucleation sites including at least one noble metal;
the composition of matter characterized by catalyzing the reduction of at least one metallic cationic species to a reduced metal, thereby plating said fibers with said reduced metal.

In addition, said publication teaches and claims processes for producing said products.

A preferred process for preparing a metallized textile according to said publication comprises the steps of:
(a) selecting a textile, in a form selected from the group consisting of yarn and fabric, said textile including fibers selected from the group consisting of natural fibers, synthetic cellulosic fibers, regenerated protein fibers, acrylic fibers, polyolefin fibers, polyurethane fibers, vinyl fibers, and blends thereof;
(b) soaking said textile in a solution containing at least one reductant cationic species having at least two positive oxidation states, said at least one cationic species being in a lower of said at least two positive oxidation states;
(c) soaking said textile in a solution containing at least one noble metal cationic species, thereby producing an activated textile; and
(d) reducing at least one oxidant cationic species in a medium in contact with said activated textile, thereby producing a metallized textile.

Said publications, however, are limited to coated fibers and textiles prepared according to said processes and do not teach or suggest the possibility of incorporating cationic copper into a polymeric slurry of a thermoplastic polymer whereby there are produced films and fibers having microscopic particles of ionic cationic copper incorporated therein and protruding therefrom and having antimicrobial, antifungal and antiviral polymeric properties, as described and exemplified herein.

In US2004/024763 there is described and claimed a process for preparing an antimicrobial and antiviral polymeric material, comprising preparing an antimicrobial and antiviral polymeric material as defined above, comprising preparing a slurry of a polymer selected from the group consisting of a polyamide, a polyester, an acrylic and a polyalkylene, and mixtures thereof, introducing a powder consisting essentially of water insoluble cationic copper oxides and dispersing the same in said slurry and then extruding said slurry to form a polymeric material wherein water insoluble copper oxide particles that release $Cu^{++}$ are encapsulated therein with a portion of said particles being exposed and protruding from surfaces thereof.

The relevant teachings of said published application and especially the antimicrobial and antiviral properties of the polymeric materials incorporating insoluble copper oxide particles that release $Cu^{++}$ are incorporated herein.

While said process was effective for small scale production of the products defined and claimed in said application, it was found that problems were encountered in industrial scale-up.

More particularly it was found that the water insoluble copper oxide particles that release $Cu^{++}$ are very reactive and therefore formed copper coatings and build-up on metal reactor walls as well as on the metal of the extruder.

The present invention is therefore directed to an improvement on and modification of said process.

In addition it is an object of the present invention to provide additives to a master batch which make it possible to enhance extrusions of fiber, injection molded products, extrusions of film, or a plastic sheets and which are easy to prepare and have improved efficacy compared to the prior art.

Suitable thermoplastic resins incorporating copper oxide and these additives include: polyethylene, polypropylene, polyester, polystyrene, polyoxymethylene, polyethylene terephthalate, polybutylene terephthalate, polymethyl methacrylate, polyether sulfones, polysulfones, polyether ketones, polystyrene copolymers, acrylonitrile-butadiene-styrene terpolymers, polyamides such as nylon 6 or nylon 6.6, polyvinyl chloride and copolymers of ethylene.

The thermoplastic resin to be modified and the carrier polymer of the masterbatch can be the same, but do not have to be.

More specifically, the present invention in its first aspect, relates to a polymeric master batch for preparing an antimicrobal and antifungal and antiviral polymeric material comprising a slurry of thermoplastic resin, an antimicrobal and antifungal and antiviral agent consisting essentially of water insoluble particles of ionic copper oxide, a polymeric wax and an agent for occupying the charge of said ionic copper oxide.

Thus according to the present invention, it has been found that the inclusion of a polymeric wax in the master batch, wets the oxide, keeps the same mobile in the wax, and prevents agglomeration therefore contributing to the formation of discreet particles of copper oxide while the agent for occupying the charge of said ionic copper oxide prevents the same from coating out on metal surfaces during the production process.

In preferred embodiments of the present invention there is provided a polymeric master batch comprising between about 4% and 83% of a thermoplastic resin, about 10%-60% on a weight basis of water insoluble particles of ionic copper oxide, between about 1% and 30% of a polymeric wax, and between about 1% and 6% of an agent for occupying the charge of said ionic copper oxide.

Particle size of the inorganic metal oxide is not a factor in being able to produce this product. This means that nanoparticles that are classically very small, for example 200-300 nano-meters in size which are very common, can also be used to obtain the same effect. It is likely that even smaller particles can be used but are less cost effective. The limiting factor is in how large the size of the particle is simply because it becomes difficult to either flow the melted master batch through the holes of a spinneret, in an extruder, or under a knife coater.

A critical prerequisite for the usability of such an additive concentrate is the correct choice of the wax component. Although it is not colored itself, it influences the performance of the additive concentrate. For more detailed information, reference may be made, for example, to the product brochure "Luwaxe®-Anwendung in Pigmentkonzentraten" about polyethylene waxes from BASF AG.

The copper based system are a dry powder with the potential to form agglomerates that have to be wetted well by the wax to prevent clumping together of the agglomerates. A small number of relatively large additive agglomerates make less contribution to the additive power of the material concerned than does a larger number of smaller additive agglomerates.

It is therefore an objective to allow no large additive agglomerates to be formed during the formulation process. Furthermore, it is desirable to separate any previously formed agglomerated additive and to split them up into their primary particles. Finally, the primary particles should also remain separated after the formulation process and not reagglomerate during cooling.

To achieve this, the wax has to meet a number of requirements. One of these requirements concerns the viscosity of the melt. The viscosity of the melt should be as low as possible so that the molten wax can readily penetrate the voids within the agglomerates of the additive during formulation, which is usually carried out by mixing at a temperature above the melting point of the wax. As a result of the shear forces applied in this way, the agglomerates are more readily split up into the primary particles.

The wetting capability of the waxes should also be good.

Polar groups can in principle be introduced into a wax by means of various process steps.

One method is to incorporate differing types of waxes including copolymers of polyethylene wax and maleic anhydride. These can be also used with ionomers of low molecular weight waxes.

In a preferred embodiment of the present invention said agent is selected from the group consisting of a chelating agent, and a metal deactivating agent.

Preferably said agent is selected from the group consisting of a metal deactivating phosphyte, a phenolic antioxidant, potassium iodide, potassium bromide, calcium stearate, zinc stearate, aluminium stearate, tertiary chain extenders and combinations thereof.

In especially preferred embodiments said agent is a metal deactivator.

In other preferred embodiments said agent is a phenolic antioxidant.

Among those agents that can be used in the present invention, there are included:

2',3-bis[[3-[3,5-di-tert-butyl-4-hydroxyphenyl]propionyl]]propionohydrazide marketed under the name Irganox® MD 1024 by CIBA;

Vitamin E (alpha-tocopherol) which is a high molecular weight phenolic antioxidant, marketed under the name Irganox® E 201 by CIBA;

Irganox® B 1171, marketed by CIBA, which is a blend of a hindered phenolic antioxidant and a phosphite, having the formulas

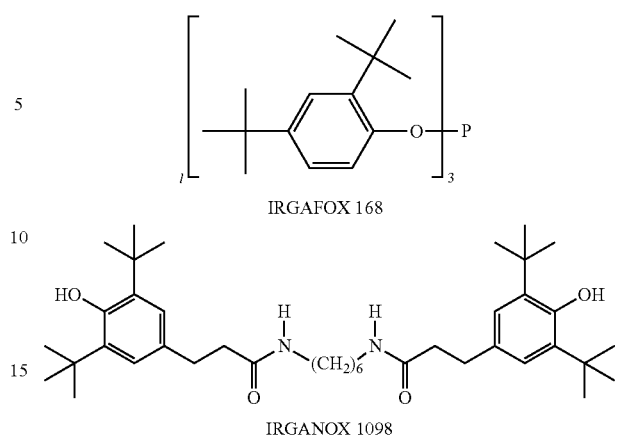

IRGAFOX 168

IRGANOX 1098

Irganox® B 501W, marketed by CIBA, which is a combination of phosphonic acid, [[3,5-bis(1,1-dimethylethyl)-4-hydroxyphenyl]methyl]-monoethylester, calcium salt; polyethylene wax and phenol, 2,4-bis(1,1-dimethylethyl)-phosphate;

Irganox® 1098 marketed by CIBA, which is a sterically hindered phenolic antioxidant having the chemical name: N,N'-hexane-1,6-diylbis(3-(3,5di-tert-butyl-4-hydroxyphenylpropionamide));

Irganox® 245, marketed by CIBA, which is a sterically hindered phenolic antioxidant having the chemical name: ethylenebis(oxyethylene)bis-(3-(5-tert-butyl-4hydroxy-m-tolyl)-propionate);

1,3,5-tris(4-tert-butyl-3-hydroxy-2,6-dimethylbenzyl)-1,3,5-triazine-2,4,6-(1H,3H,5H)trione, which is an antioxidant marketed by CYTEC Industries as Cyanox® 1790;

1,3,5-trimethyl-2,4,6-tris(3,5-di-tert-butyl-4-hydroxybenzyl)benzene, which is a high-performance phenolic antioxidant marketed by AMBEMARLE Corp. as Ethanox® 330;

1,3,5-tris(3,5-di-tert-butyl4-hydroxybenzyl)-1,3,5-ritazine-2,4,6(1h,3h,5h)-trione, which is a phenolic antioxidant-marketed by AMBEMARLE Corp. as Ethanox® 314;

penterythritol telraks(3-(3,5-di-t-butyl-4-hydroxyphenol) propionate), which is a phenolic antioxidant marketed by AMBEMARLE Corp. as Ethanox® 310;

octadecyl-3-(3,5-di-t-butyl-4-hydroxyphenyl)propionate, which is an antioxidant marketed by AMBEMARLE Corp. as Ethanox® 376;

4,4'-methylenebis(2,6-di-tertiary-butylphenol), which is an antioxidant marketed by AMBEMARLE Corp. as Ethanox® 702;

2,6-di-tertiary-butyl-n,n-dimethylamino-p-crescl, which is an antioxidant marketed by AMBEMARLE Corp. as Ethanox® 703;

tris-(2,4-di-t-butylphenyl)phosphite, which is a phosphite antioxidant marketed by AMBEMARLE Corp. as Ethaphos® 368.

Chelating agents that can be used in the present invention, include such compounds as:

Diethylenetriaminepentaacetic acid (dtpa)
Ethylenedinitrilotetraacetic acid (edta)
Nitrilotriacetic acid (nta)
Ethylenediamine (eda)
Diethyltriamene (deta)
Triethylenetetraamine (teta)

Tetraethylenepentamine-UHP (tepa-UHP)
Pentaethylenehexamine (peha)
Piperazine
and mixtures thereof.

Preferably said thermoplastic resin is selected from the group consisting of a polyester, a polyolefin, a nylon, a polyurethane, polytetrafluoroethylene, polypropylene, polyethylene, polyvinyl chloride, an acrylic, polybutylene, polylactic acid, PTT, a silicon and mixtures thereof.

In preferred embodiments said polymeric wax is selected from the group consisting of homopolymers, oxidized homopolymers, high density oxidized homopolymers and co-polymers of polyethylene, polypropylene and ionomer waxes, micronized polyolefin waxes and mixtures thereof, as well as co-polymers of ethylene-acrylic acid and ethylene-vinyl acetate.

Especially preferred are waxes selected from the group consisting of a polypropylene wax marketed by Clariant as Licowax PP 230, an oxidized polyethylene wax marketed by Clariant as Licowax PED 521, an oxidized polyethylene wax marketed by Clariant as Licowax PED 121, as well as an ethylene homopolymer wax marketed by BASF as Luwax®.

In another aspect of the present invention there is now provided a process for preparing an antimicrobial, antifungal and antiviral polymeric material, comprising preparing a slurry of a thermoplastic resin, introducing a powder consisting essentially of water insoluble cationic copper oxides and dispersing the same in said slurry in combination with a polymeric wax and an agent for occupying the charge of said ionic copper oxide and then extruding said slurry to form a polymeric material wherein discreet water insoluble copper oxide particles that release $Cu^{++}$ are formed and incorporated therein with a portion of said particles being exposed and protruding from surfaces thereof.

Preferably said combination of ingredients is carried out with high intensity mixing for a period of about 5-15 minutes and at a temperature of between 120° C. and 180° C.

In an especially preferred embodiment of the present invention said process comprises combining between about 4% and 83% of a thermoplastic resin, about 10%-60% on a weight basis of water insoluble particles of ionic copper oxide, between about 1% and 30% of a polymeric wax, and between about 1% and 6% of an agent for occupying the charge of said ionic copper oxide.

In preferred embodiments of said process said agent is selected from the group consisting of a chelating agent and a metal deactivating agent.

Preferably said agent is selected from the group consisting of a metal deactivating phosphyte, a phenolic antioxidant, potassium iodide, potassium bromide, calcium stearate, zinc stearate, aluminium stearate, tertiary chain extenders and combinations thereof.

In an especially preferred embodiment said agent is a metal deactivator.

In especially preferred embodiment said agent is a phenolic antioxidant.

Preferably in said process said thermoplastic resin is selected from the group consisting of a polyester, a polyolefin, a nylon, a polyurethane, polytetrafluoroethylene, polypropylene, polyethylene, polyvinyl chloride, an acrylic, polybutylene, polylactic acid, PTT, a silicon and mixtures thereof.

In said process said polymeric wax is preferably selected from the group consisting of consisting of homopolymers and co-polymers of polyethylene, polypropylene and Ionomer waxes, and mixtures thereof.

In a further aspect of the present invention there is provided an antimicrobial, antifungal and antiviral polymeric material whenever produced according to the process defined and claimed herein, said material being in the form of a fiber, a yarn, or a sheet and comprising an antimicrobial, antifungal and antiviral agent consisting essentially of discreet water insoluble ionic copper oxide particles that release $Cu^{++}$ incorporated therein with a portion of said particles being exposed and protruding from surfaces thereof.

Preferably in said antimicrobial and antiviral polymeric material the ionic copper comprises a mixture of $CuO$ and $Cu_2O$.

In especially preferred embodiments of the present invention said particles are of a size of between 0.2 to 20 microns.

Preferably said particles are present in an amount of between 0.25 and 5% of the polymer weight.

In some preferred embodiments of the present invention said thermoplastic resin is a single polymeric component.

In some embodiments of the present invention, said polymeric material is manufactured in the form of a short staple fiber.

The invention also provides a blended yarn incorporating fibers produced according to the process of the present invention.

Also provided is a bi-component yarn wherein at least one of the components is an antimicrobial and antiviral polymeric material produced according to the process of the present invention.

The invention also provides an article of clothing incorporating a yarn which includes an antimicrobial and antiviral polymeric material produced according to the process of the present invention.

Also provided according to the present invention is a wrapping material comprising an antimicrobial polymeric material produced according to the process of the present invention.

In another preferred embodiment of the present invention, there is provided a carpet having an antimicrobial and antiviral polymeric material produced according to the process of the present invention incorporated into a backing layer thereof.

The invention also provides a non-woven molded product having an antimicrobial and antiviral polymeric material produced according to the process of the present invention incorporated therein.

Preferably said non-woven molded product is air permeable, and can be either hydrophobic or hydrophilic by post treatment of the finished non-woven material.

In other preferred embodiments said non-woven molded product is liquid permeable.

In U.S. Pat. No. 6,482,424 there is described and claimed textile fabrics for combating nosocomial infections in health care facilities, said fabric incorporating fibers coated with a $Cu^{++}$ cationic form of copper for use in patient contact and care, wherein said textile fabric is effective for the inactivation of Methicillin Resistant *Staphylococcus aureus* and Vancomycin Resistant Enterococci, or any of the newer antibiotic strains appearing worldwide. These could include viral based diseases such as SARS (Severe Acute Respiratory Syndrome) or the more recent Avian Viruses.

The relevant teachings of said patent are incorporated herein since it has now been found that polymeric materials according to the present invention also exhibit this same activity against nosocomial infections.

Therefore in another aspect of the present invention there are provided textile fabrics for combating nosocomial infections in health care facilities, said fabric incorporating a fiber, a yarn, or a sheet and comprising an antimicrobial and antiviral agent consisting essentially of discreet water insoluble copper oxide particles that release $Cu^{++}$ incorporated therein with a portion of said particles being exposed and protruding from surfaces thereof whenever produced according to the process of the present invention.

The present invention is also directed to the use of a polymeric material produced from a master batch as defined and claimed herein, for inhibition of HIV-1 proliferation.

The present invention is also directed to the use of a polymeric material produced from a master batch as defined and claimed herein for neutralizing infectious viruses.

In other aspects of the present invention there are provided condoms, catheters, filters and gloves whenever produced from a master batch according to the present invention.

Also provided according to the present invention are non-woven fabrics whenever produced from a polymeric master batch comprising a thermoplastic resin, water insoluble particles of ionic copper oxide, a polymeric wax and an agent for occupying the charge of said ionic copper oxide.

Also provided according to the present invention are disposable diapers incorporating a non-woven fabric as defined above.

In especially preferred embodiments of the present invention there are provided disposable hospital and operating theatre products for combating viral infections, said products incorporating fibers produced from a master batch as defined above wherein said fibers are effective for the inactivation of viruses and fluids brought in contact therewith.

Preferably said products are selected from the group consisting of disposable scrubs, barriers, clothing, masks, shoe covers and caps.

In preferred embodiments of the present invention, said fibers are disposed in said products as randomly scattered fibers in a non-woven textile.

The invention also provides a device for the inactivation of a virus comprising a housing delimiting a fluid passageway, said passageway being provided with a filtering material including polymeric fibers comprising an antimicrobial, antifungal and antiviral agent consisting essentially of discreet water insoluble ionic copper oxide particles that release $Cu^{++}$ incorporated therein with a portion of said particles being exposed and protruding from surfaces thereof, wherein said fibers are produced from a master batch according to the present invention.

In preferred embodiments of said device, said fluid is either a liquid or air containing breath moisture.

In preferred embodiments of said device said discreet ionic water insoluble copper particles are incorporated in fibers in a non-woven fabric.

In especially preferred embodiments of the present invention there is provided a device for inactivating a virus found in cells in body fluids wherein said device comprises a filtering material including polymeric fibers comprising an antimicrobial, antifungal and antiviral agent consisting essentially of discreet water insoluble ionic copper oxide particles that release $Cu^{++}$ incorporated therein with a portion of said particles being exposed and protruding from surfaces thereof, wherein said fibers are produced from a master batch according to the present invention.

The polymeric material of the present invention can be in the form of a film, a fiber, or a yarn, wherein said films can be used per se, e.g. for wrapping and for forming articles of manufacture such as gloves, condoms, blood storage bags, catheters and other forms of tubing or can be cut into fine strips, woven into a substrate to form a backing for a carpet by punching said substrate with carpet pile. Said fibers and yarns can be formed into a packaging material for agricultural products or into a non-woven molded product, such as a non-woven mask, an air filter for a hospital or airplane, or a gauze. Similarly the polymeric materials of the present invention can be mixed with other fibers or materials and used to prepare feminine hygiene products, diapers, shoe-lining material, articles of clothing, sheets, pillow cases, barrier fabrics, etc.

Similarly as stated hereinbefore said polymer can be in a continuous, flat, textured or stretched form which can be used in articles of clothing, etc.

Said material can be made from almost any thermoplastic polymer, which will allow the introduction of an cationic, copper oxide particles into its liquid slurry state. Examples of some materials are polyester, a polyolefin, a nylon, a polyurethane, polytetrafluoroethylene, polypropylene, polyethylene, polyvinyl chloride, an acrylic, polybutylene, polylactic acid, PTT, a silicon and mixtures thereof. When the copper oxide dust is ground down to fine powder, e.g., a size of between 0.2 and 20 microns and introduced into the slurry in small quantities, e. g., in an amount of between 0.25 and 5% of the polymer weight, it was found that the subsequent product produced from this slurry exhibited both antimicrobial and antiviral properties. It is also possible to increase the surface area of the particulate by including a small particle such as a nano sized particle for inclusion in the formula.

As described hereinbefore in a further preferred embodiment of the present invention said polymeric material is manufactured in the form of a short staple fiber and the present invention is also directed to a blended yarn incorporating such fibers.

In yet another preferred embodiment of the present invention there is provided a bi-component yarn wherein at least one of the components is an antimicrobial and antiviral polymeric material produced from the master batch of the present invention.

The present invention also provides an article of clothing incorporating a yarn which includes an antimicrobial and antiviral polymeric material produced from the master batch of the present invention.

In further preferred embodiments of the present invention pigments can be added to the master batch as defined herein, in order to form a paint, as known per se, with the added properties of being antifungal and antibacterial, and therefore being useful in healthcare settings, as well as for preventing mold formation in all settings.

In yet other preferred embodiments of the present invention, the polymeric materials produced from a master batch as defined herein, can be incorporated into therapeutic and cosmetic topical creams, lotions and ointments by methods known per se, including encapsulating the same with time release coatings.

Encapsulation technologies abound in the market place. Methods for preparing a controlled, delayed release encapsulate triggered by a time release, or pressure release or dissolving release of the encapsulate are common in both the food/medicine and cosmetic industries. These encapsulates are usually made from a water insoluble matrix which are applied to a ground solid base targeted powder, the introduction of the insoluble matrix in liquid form is exposed to the base powder which it coats. This coating will prevent elusion of the base powder and will not dissolve under the hydrolytic condition of an oil or hand cream or food additive until they are rubbed in the hands and burst in the case of the hand cream or chewed in the case of the medicine. These types of techniques are common in many industries for chemical time release and are well known to those familiar with these arts.

Unlike the fibers described, e. g. in WO 98/06508 and WO 98/06509, in which the fibers are coated on the outside, in the present product the polymer has microscopic water insoluble particles of cationic copper oxide incorporated therein with a portion of said particles being exposed and protruding from surfaces thereof. These exposed particles which protrude from the surface of the polymeric material have been shown to be active.

In WO 94/15463 there are described antimicrobial compositions comprising an inorganic particle with a first coating providing antimicrobial properties and a second coating providing a protective function wherein said first coating can be silver or copper or compounds of silver, copper and zinc and preferred are compounds containing silver and copper (II) oxide. Said patent, however, is based on the complicated and expensive process involving the coating of the metallic compositions with a secondary protective coating selected from silica, silicates, borosilicates, aluminosilicates, alumina, aluminum phosphate, or mixtures thereof and in fact all the claims are directed to compositions having successive coatings including silica, hydrous alumina and dioctyl azelate.

In contradistinction, the present invention is directed to the use and preparation of a polymeric material, having microscopic discreet water insoluble particles of cationic copper oxide in powder form, which release $Cu^{++}$ incorporated therein with a portion of said particles being exposed and protruding from surfaces thereof, which is neither taught nor suggested by said publication and which has the advantage that the exposed $Cu^{++}$ releasing water insoluble particles which protrude from the polymeric material have been proven to be effective even in the inhibition of HIV-1 activity.

In EP 427858 there is described an antibacterial composition characterized in that inorganic fine particles are coated with an antibacterial metal and/or antibacterial metal compound and said patent does not teach or suggest a polymer that incorporates discreet microscopic water insoluble particles of cationic copper oxide in powder form, which release $Cu^{++}$ encapsulated therein with a portion of said particles being exposed and protruding from surfaces thereof.

In DE 4403016 there is described a bacteriacidal and fungicidal composition utilizing copper as opposed to ionic $Cu^{++}$ and said patent also does not teach or suggest a polymer that incorporates discreet microscopic water insoluble particles of cationic copper oxide in powder form, which release $Cu^{++}$ encapsulated therein with a portion of said particles being exposed and protruding from surfaces thereof.

In JP-01 046465 there is described a condom releasing sterilizing ions utilizing metals selected from copper, silver, mercury and their alloys which metals have a sterilizing and sperm killing effect, wherein the metal is preferably finely powdered copper. While copper salts such as copper chloride, copper sulfate and copper nitrate are also mentioned, as is known, these are water soluble salts which will dissolve and break down the polymer in which they are introduced. Similarly, while cuprous oxide is specifically mentioned, this is a $Cu^+$ ionic form, and not the $Cu^{++}$ form.

The distinction between the $Cu^+$ ionic form and the $Cu^{++}$ ionic form is clear. Further, in experiments conducted on behalf of the Applicant, CuO powder (releasing $Cu^+$) was not effective as an antibacterial agent against *E. coli* or *Staphylococcus aureus* bacteria while, surprisingly $Cu_2O$ (releasing $Cu^{++}$) was effective and, surprisingly, the combination of $Cu_2O$ and CuO was even more effective that $Cu_2O$ by itself. The experiments used the ATCC Test Method 47, in which a zone of inhibition created around a one gram sample on a semi-wet agar is measured. Oyamada described neither the use of discreet particles of $Cu_2O$ (releasing $Cu^{++}$) nor the use of $Cu_2O$ and CuO in combination, as is instantly claimed and cannot anticipate the invention.

It is further to be noted that in working example 1 in table 1 of said patent, there is mentioned copper oxide although the nature of the copper oxide mentioned is not clarified. Even if one were to assume, for argument's sake, that this example refers to the use of a cupric oxide, it is to be noted that in this example, the cupric oxide is provided together with an organopolysiloxane and thus persons skilled in the art understand that this copper was cross-linked to the polymer chain and did not exist as free discreet particles.

As will therefore be realized, said patent also does not teach or suggest the use of discreet, exposed, $Cu^{++}$ releasing water insoluble particles which protrude from the polymeric material and which have been proven to be effective in the reduction of oral bacteria.

In JP-01 246204 there is described an antimicrobial molded article in which a mixture of a powdery copper compound and organic polysiloxane are dispersed into a thermoplastic molded article for the preparation of cloth, socks, etc. Said patent specifically states and teaches that metal ions cannot be introduced by themselves into a polymer molecule and requires the inclusion of organopolysiloxane which is also intended to provide a connecting path for the release of copper ions to the fiber surface.

Furthermore, also in this patent, the copper powder is introduced simultaneously with the organopolysiloxane which results in the copper being cross-linked within the polymeric material and not existing as discreet free water insoluble particles of copper oxide that protrude from the polymeric material and release $Cu^{++}$. Further, Oyamada did not describe or teach the use of a polymeric wax and an agent for occupying the charge of cupric oxide in the master batch and the advantages inherent therein.

In JP-03 113011 there is described a fiber having good antifungus and hygienic action preferably for producing underwear wherein said synthetic fiber contains copper or a copper compound in combination with germanium or a compound thereof, however, said patent teaches and requires the presence of a major portion of germanium and the copper compounds disclose therein are preferably metallic copper, cuprous iodide which is a monovalent $Cu^+$ compound and water soluble copper salts. Thus, said patent does not teach or suggest the use of exposed $Cu^{++}$ releasing water insoluble copper oxide particles which protrude from the polymeric material or teach the use of a polymeric wax and an agent for occupying the charge of cupric oxide in the master batch and the advantages inherent therein.

In EP 116865 there is described and claimed a polymer article containing zeolite particles at least part of which retain at least one metal ion having a bacterial property and thus said patent does not teach or suggest the use of exposed $Cu^{++}$ releasing water insoluble copper oxide particles, by themselves and in the absence of a zeolite, which particles protrude from the polymeric material and also does not teach or suggest the use of a polymeric wax and an agent for occupying the charge of cupric oxide in the master batch and the advantages inherent therein In EP 253653 there is described and claimed a polymer containing amorphous aluminosilicate particles comprising an organic polymer and amorphous aluminosilicate solid particles or amorphous aluminosilicate solid particles treated with a coating agent, at least some of said amorphous aluminosilicate solid particles holding metal ions having a bactericidal actions. Thus, said patent does not teach or suggest the use of exposed $Cu^{++}$ releasing water insoluble copper oxide particles, by themselves and in the absence of amorphous aluminosilicate particles, which exposed $Cu^{++}$ releasing water insoluble copper oxide particles, protrude from the polymeric material, or teach the use of a polymeric wax and an agent for occupying the charge of cupric oxide in the master batch and the advantages inherent therein In U.S. Pat. No. 5,180,402 there is described and claimed a dyed, synthetic fiber comprising silver-substituted zeolite and a copper compound and processes for the preparation thereof and said patent claims a dyed synthetic polyamide fiber having antibacterial and antifungal properties, which comprises based on the weight of the fiber, 0.01-20% by weight of a silver-substituted zeolite exhibiting antibacterial and antifungal action, and 0.001-1% by weight of a substantially water-insoluble copper compound.

Said patent, however, specifically teaches the incorporation of the water-insoluble copper to prevent the reduction of the antibacterial action of the silver-substituted zeolite during dyeing and in Table 1, said patent specifically teaches that in fabrics in which the silver-substituted zeolite was not incorporated, the fiber which contained copper alone did not exhibit an antibacterial property.

Thus said patent constitutes a specific teaching away from the teachings of the present invention.

In U.S. Pat. No. 5,736,591 to Dunn, there is described and claimed a latex with resistance to bacterial growth wherein the method for inhibiting the growth of bacteria in latex comprises incorporating therein ions of a metal from Group IB in the Periodic Chart which group contains a series of metal and metal oxides which include silver, copper, and gold. The patent itself however only makes claims regarding silver along with test data to support the use of silver. There is no question the test data and the methods used in the patent for adding silver to the latex is effective and chemically correct. However, this would not apply to any copper compound in any latex compound. Someone skilled in the chemistry of latex would know that the elasticity and strength of latex stems from a zinc cross linked bond. Silver does not have the same reduction capacity of copper in latex and will therefore have a much smaller effect on the linkage. The appearance of any copper oxide at all is known to reduce zinc and to weaken the bond. This reduction would have the effect of weakening the latex and would render the latex too weak to be used for normal commercial uses. If the inventor were to substitute copper or copper oxide for the silver in the formula discussed, he would find an unsuccessful creation of a latex product. The product simply would have no elasticity or strength. No one has yet been able to add a copper compound to latex and still retain the same qualities as when it has no additives. Therefore this patent does not teach or suggest a polymeric batch as defined herein.

U.S. Pat. No. 5,976,562 to Krall et al., relates to a process for producing bactericidal/fungicidal plastic bodies. In said patent there is a discussion regarding the formation of a thin film on a plastic which contains a metal oxide thus imparting an antimicrobial quality to the injection molded plastic part. In this patent the coating is the actual metal oxide which is used to line the inside of a mold so that when the plastic is injected into the mold the metal oxide is incorporated on the outside layer of the object. In the present application, the copper metal oxide is encapsulated and is incorporated into the actual polymer, and not just as an outside coating, as taught and suggested by this reference.

US Patent Application No: 2004/0259973 to Sakuma et al describes and claims antibacterial composite particles and an antibacterial resin composition comprising a thermoplastic polymer based material and a phosphate salt compound. In said patent a preferred embodiment comprises a phosphate salt compound carrier having an antibacterial metal carried thereon, wherein said antibacterial metal is selected from silver, copper and zinc. In said patent when a metal oxide is used the metal oxide is attached to a ceramic compound in order to allow its inclusion in a master batch. The inorganic particles are formed by carrying a metallic ion on an inorganic ceramic carrier. Since the above patent application is limited to the teaching of the use of a ceramic carrier and the necessary inclusion of a phosphate salt and since the present invention does not use the same said publication is relating to a completely different technology than that described and taught in the present specification.

US Patent Application No: 2005/0065231 to Sasaki et al, is directed to inorganic antimicrobial agents, antimicrobial molded resin articles using the same and processes for the production thereof. In said patent the inorganic antibacterial particles preferably comprise a metal and inorganic carrier and include a metal selected from silver, copper, zinc, gold, platinum and nickel. In a preferred embodiment the inorganic antibacterial particles comprise calcium phosphate carrying at least one metal selected from silver and zinc. It is to be noted however, that the metals are elemental metals, not metal oxides. In addition, they are attached to a ceramic compound which acts as a carrier. In contradistinction, the present invention does not use an elemental metal nor does it involve the use of a ceramic carrier for the creation of the active compound in a master batch.

In US Patent Application No: 2005/0124724 to Burton et at there is described and claimed polymer compositions with bioactive agents, medical articles and methods wherein the bioactive agent is selected from the group consisting of a silver compound, a copper compound, a zinc compound and combinations thereof. This patent refers to a hydrophilic polymer that uses a secondary organic polymer as a carrier. The secondary polymer also acts as a binding agent between the hydrophilic polymer and the inorganic metal oxide. In contradistinction in the present application, the copper oxide directly interacts with the main component thermoplastic resin and therefore said reference also does not teach or suggest the subject matter of the present invention. Furthermore, in this application the basis of all the polymers is that they are hydrophilic. In this case, the density of each polymer is controlled by the amount of water in the compound. In the case of polymers referred to in the present application, water is a forbidden element as it destroys the ability of the polymer to link. As such, said U.S. application is directed to a subject which is completely different than that of the present invention.

U.S. Pat. No. 4,911,899 Hagiwara el al discusses zeolite particles having bacteriocidal properties. As an aside said patent mentions silver, copper and zinc as well. However, the present invention does not involve the use of a zeolite and the mechanism taught in said patent utilizing the same is not utilized in the present invention. Therefore, this patent does not teach or suggest the presently claimed subject matter.

U.S. Pat. No. 5,503,840 Jacobson et at is directed to antimicrobial compositions consisting essentially of coated core particles, wherein the core particles consist essentially of a mixture of at least two members selected from the group consisting of titania, barium sulphate and zinc oxides, wherein said core particles are successively with successive coatings of silver and further coatings of zinc and/or copper compounds such as zinc oxide, copper oxide and a series of other coatings. In contradistinction the present invention is directed to the use of a powder consisting essentially of water insoluble cationic copper oxides as a stand-alone compound functioning as the sole active ingredient and does not involve a coating combined with a combination of different anti-microbials in a polymer. Thus, said patent is also very different than the subject matter of the present invention and does not teach or suggest the same.

U.S. Pat. No. 6,585,989 B2 Herbst et al discusses the use of organic anti-microbials in a polymer and therefore said patent does not teach or suggest the present subject matter.

U.S. Pat. No. 5,180,585 to Jacobson et al discloses an antimicrobial powder composition comprising inorganic particles having a primary surface coating having a metal or metal compound and a secondary coating providing a protective function such as silica and alumina or alumina by itself. Thus, said patent is directed to an inorganic particle with a first coating providing antimicrobial properties and a second coating providing a protective function which secondary coating functions as a barrier between the antimicrobial particle and a polymer matrix in which it may be incorporated for minimizing interactions with the polymer. In contradistinction, the present invention is directed to water insoluble particles of ionic copper oxide which are directly incorporated within the polymeric master batch without any protective coating or core element.

U.S. Pat. No. 5,478,563 to Erami, refers to a polyacetal resin using a combination of silver, copper, and zinc ions and therefore this publication also does not teach or suggest the subject matter of the present invention.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

A. General Procedure

1. A slurry is prepared from any polymer, the chief raw material preferably being selected from a polyamide, a polyalkylene, a polyurethane and a polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 80 to 150° C.

2. At the hot mixing stage, before extrusion, a water insoluble powder of cationic copper oxide is added to the slurry and allowed to spread through the heated slurry. The particulate size will be preferably between 0.2 to 20 microns, however can be larger when the film or fiber thickness can accommodate larger particles.

3. The liquid slurry is then pushed with pressure through holes in a series of metal plates formed into a circle called a spinneret. As the slurry is pushed through the fine holes that are close together, they form single fibers or if allowed to contact one another, they form a film or sheath. The hot liquid fiber or film is pushed upward with cold air forming a continuous series of fibers or a circular sheet. The thickness of the fibers or sheet is controlled by the size of the holes and speed at which the slurry is pushed through the holes and upward by the cooling air flow.

4. In percentage mixtures of up to 5% by weight of cationic copper oxide dust demonstrated, no degradation of physical properties in a polymeric slurry of the finished product.

Comparative Example 1

Using the method described above, the following components were combined and processed:

| | | |
|---|---|---|
| 1. | copper oxide | 10-60% on a weight basis |
| 2. | a polymer wax type material consisting of homopolymers and co-polymers of polyethylene, polypropylene and Ionomer waxes, and mixtures thereof | 1-30% |
| 3. | thermoplastic resin | 10-89% |

Said components were subjected to high intensity mixing for 2 to 10 minutes at a temperature of 80 to 150° C. and then extruded through a twin screw extruder.

There was observed a plating out of copper on metal surfaces and a high rise in pressure within the system.

Example 2

The procedure of example 1 was repeated with the following components:

| | | |
|---|---|---|
| 1. | copper oxide | 10-60% on a weight basis |
| 2. | a polymer wax type material consisting of homopolymers and co-polymers of polyethylene, polypropylene and Ionomer waxes, and mixtures thereof. | 1 to 30% |
| 3. | thermoplastic resin | 4-83% |
| 4. | Irgafoss 3114 (a phenolic antioxidant) | 1-6% |

Said components were subjected to high intensity mixing for 2 to 10 minutes at a temperature of 80 to 150° C. and then extruded through a twin screw extruder.

With these ingredients there was no plating out on the screens or on the equipment and the pressure rise was significantly reduced.

Example 3

Preparation of Yarns and Fibers from a Master Batch

A1. A master batch is prepared according to example 2 using the same base material as the desired yarn into which a copper oxide powder is added. For most textile end uses the master batch will preferably have a 10%-60% concentration of the copper oxide powder included in it. This master batch is added to the polymer being extruded and diluted so that only about 0.25% to 5% of the material will be in the finished yarn. A certain amount of this copper will appear on the surface of a polymeric fiber and can be observed in an electron microscope picture.

A2. If the fiber is a filament fiber it can be applied to a multiplicity of uses including formation as a yarn which is an extruded filament produced as in A1 from a plurality of fibers through a spinaret.

A3. For the manufacture of staple fibers: The same basic process is followed for the creation of a staple (short or long, not continuous) filament fiber as per the formation described above. However, a variation of these fibers can be created to form a staple fiber rather than continuous fiber. The formation of a staple fiber of varying physical qualities can be extruded to any thickness and cut to any length. The creation of these fibers will facilitate blending treated fibers into any spun yarn product whether short staple, as in cotton, or long staple as in wool or any other fiber blends in any proportion desired comprised of different fibers.

Thus as will be realized, the difference between the normal process of manufacturing polymeric products and the process of the present invention, is the addition of microscopic $Cu^{++}$ releasing water insoluble particles into the polymeric raw materials in the presence of a polyethylene wax and in the presence of an agent for occupying the charge of the cupric oxide.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process of preparing an antimicrobial, antifungal and antiviral polymeric material, comprising:
   preparing a master batch composition, wherein the master batch composition is in the form of an extruded solid and the master batch composition consists essentially of:
   about 4% to about 83% of a thermoplastic resin;
   about 10% to about 60% of an antimicrobial, antifungal and antiviral agent consisting essentially of discrete water insoluble particles of cationic copper oxide;
   about 1% to about 30% of a polymeric wax; and
   about 1% to about 6% of an agent for occupying the charge of said ionic copper oxide,
   wherein wt % is based on the total weight of the composition; and
   combining the master batch composition with a thermoplastic composition to form a combined thermoplastic composition; and
   extruding the combined thermoplastic composition to form an antimicrobial, antifungal and antiviral polymeric material,
   wherein discrete water insoluble particles of ionic copper oxide that release $Cu^{++}$ are exposed and protrude from a surface of the polymeric material.

2. A process of preparing an antimicrobial, antifungal and antiviral polymeric material, comprising:
   preparing a master batch composition, wherein the master batch composition is in the form of an extruded solid and the master batch composition consists essentially of:
   about 4% to about 83% of a thermoplastic resin;
   about 10% to about 60% of an antimicrobial, antifungal and antiviral agent consisting essentially of discrete water insoluble ionic copper oxide particles of CuO and $Cu_2O$;
   about 1% to about 30% of a polymeric wax; and
   about 1% to about 6% of an agent for occupying the charge of said ionic copper oxide,
   wherein wt % is based on the total weight of the composition; and
   combining the master batch composition with a thermoplastic composition to form a combined thermoplastic composition; and
   extruding the combined thermoplastic composition to form an antimicrobial, antifungal and antiviral polymeric material,
   wherein discrete water insoluble particles of ionic copper oxide that release $Cu^{++}$ are exposed and protrude from a surface of the polymeric material.

3. The process of claim 1, wherein the discrete water insoluble particles of ionic copper oxide are characterized by a size between 0.2 microns and 10 microns.

4. The process of claim 1, wherein the combined thermoplastic composition comprises the discrete water insoluble particles of ionic copper oxide in a range from 0.25 wt % and 5 wt %, wherein wt % is based on the total weight of the polymeric material.

5. The process of claim 1, wherein the polymeric wax is selected from the group consisting of homopolymers, oxidized homopolymers, high density oxidized homopolymers and co-polymers of polyethylene, polypropylene, ionomer waxes, micronized polyolefin waxes, and co-polymers of ethylene-acrylic acid, ethylene-vinyl acetate, and a combination of any of the foregoing.

6. The process of claim 1, wherein the polymeric wax is selected from the group consisting of homopolymers and co-polymers of polyethylene, polypropylene, ionomer waxes, and a combination of any of the foregoing.

7. The process of claim 1, wherein the combined thermoplastic composition is extrudable without a plating out of the water insoluble particles of ionic copper oxide on metal surfaces of an extrusion apparatus.

8. The process of claim 1, wherein the agent for occupying the charge of said ionic copper oxide is selected from the group consisting of a metal deactivating phosphite, a phenolic antioxidant, potassium iodide, potassium bromide, calcium stearate, zinc stearate, aluminum stearate, and a combination of any of the foregoing.

9. The process of claim 1, wherein the combined thermoplastic composition comprises a metal deactivator.

* * * * *